United States Patent [19]

Iida et al.

[11] Patent Number: 4,812,220
[45] Date of Patent: Mar. 14, 1989

[54] ENZYME SENSOR FOR DETERMINING A CONCENTRATION OF GLUTAMATE

[75] Inventors: Takeaki Iida, Niiza; Takeshi Kawabe, Tokyo, both of Japan

[73] Assignee: Unitika, Ltd., Hyogo, Japan

[21] Appl. No.: 84,570

[22] Filed: Aug. 12, 1987

[30] Foreign Application Priority Data

Aug. 14, 1986 [JP] Japan ................................ 61-190840

[51] Int. Cl.$^4$ ............................................. G01N 27/46
[52] U.S. Cl. ................................... 204/403; 204/418; 204/420; 435/4; 435/817
[58] Field of Search ...................... 204/403, 416–420; 435/4, 817

[56] References Cited

U.S. PATENT DOCUMENTS

| | | | |
|---|---|---|---|
| 3,776,819 | 12/1973 | Williams | 204/403 |
| 3,803,006 | 4/1974 | Krueger et al. | 204/420 |
| 3,896,008 | 7/1975 | Keyes | 204/420 |
| 4,020,830 | 5/1977 | Johnson et al. | 204/418 |

Primary Examiner—T. Tung
Attorney, Agent, or Firm—Wenderoth, Lind & Ponack

[57] ABSTRACT

Disclosed is an enzyme sensor for determining a concentration of glutamate comprising an immobilize enzyme acting specifically to a substrate and a transducer for converting the quantitative change of a substance or heat which is produced or consumed during an enzyme reaction to an electrical signal, wherein the enzyme is glutamine synthetase and the transducer is the pH glass electrode or ion-sensitive field-effect transistor (IS-FET). The enzyme sensor can be miniaturized and can accurately determine a concentration of glutamate even when it is low.

2 Claims, 4 Drawing Sheets

Concentration of glutamate ( mM )

ENZYME SENSOR FOR DETERMINING A CONCENTRATION OF GLUTAMATE

FIELD OF THE INVENTION

The present invention relates to an enzyme sensor used for determining a concentration of L-glutamate in a sample.

BACKGROUND OF THE INVENTION

A quantitative determination of L-glutamate is very important for process control or product analysis in the field of a food product industry or amino acid industry. A convenient quantitative determination of L-glutamate is also required in the field of clinical chemistry laboratories. For example, the determination is very important for a determination of the activity of glutamate-oxaloacetate transaminase (GOT) or glutamate-pyruvate transaminase (GPT) in a serum collected for a diagnosis of liver function and myocardial infarction.

In the field of the food product industry or amino acid industry, an instrumental analysis using liquid chromatography, especially an amino acid analyzer, is widely used for the quantative determination. It has been recently proposed to use determining reagents using enzymes. These methods are advantageous in easy pretreatment of a sample and accurate determination due to substrate specificity. The enzymes used for the determining reagent include glutamate dehydrogenase, glutamate oxidase, glutamate decarboxylase or the like. The determining reagent using glutamate dehydrogenase is presently commercially available. In the determination of the activity of GOT or GPT, a method wherein oxaloacetic acid or pyruvic acid is analyzed with a determining reagent containing malate dehydrogenase or lactate dehydrogenase is lately adopted. This method is also advantageous in accurate determination and easy pretreatment of a sample. However, in these methods, it takes quite a long time to determine and a life time of the determining reagent is very short.

In order to overcome the above mentioned defects, an enzyme sensor composed of an enzyme having excellent substrate specificity and an electrode has been developed. As for a L-glutamate sensor using enzymes, an enzyme sensor composed of glutamate dehydrogenase and an ammonium ion electrode is proposed. A microorganism sensor composed of an electrode and a microorganism instead of an enzyme is also studied. Presently proposed is a microorganism sensor composed of *Escherichia coli* and a carbon dioxide gas electrode (see Protein, Nucleic acid and Enzyme, volume 30, No. 4, pp. 245 to 298, 1985, especially Table 2 of pp. 262 and Table 1 of pg. 265). Further, another enzyme sensor composed of glutamate oxidase is known to the art (see Japanese patent publication (unexamined) 34882/1984). However, these sensors have problems in life time and selectivity to a substrate to be measured. In order to improve the defects, another type of enzyme sensor composed of glutamine synthetase isolated from thermophilic bacteria and an ammonia gas electrode is proposed (Denki Kagaku, 54, No. 3 (1986), 291 to 292). This sensor enhances its life time, but it is not sensitive in the region of low concentration of glutamate. It is also desired that the enzyme sensor is miniaturized as far as possible, but it is difficult to miniaturize it when an electrode made of glass is employed.

SUMMARY OF THE INVENTION

An object of the present invention is to provide an enzyme sensor for accurately determining a concentration of glutamate even when its concentration is low. The sensor can be miniaturized if desirable.

As the result of a study for accomplishing the above mentioned object, it has been found that an enzyme sensor, in which the enzyme is glutamine synthetase and the transducer is a pH glass electrode or ion-sensitive field-effect transistor (ISFET), can quickly response glutamate even when its concentration is low and can be miniaturized.

Accordingly, the present invention is to provide an enzyme sensor for determining a concentration of glutamate comprising an immobilized enzyme acting specifically to a substrate and a transducer for converting the quantitative change of a substance or heat which is produced or consumed during an enzyme reaction to an electrical signal, wherein the enzyme is glutamine synthetase and the transducer is the pH glass electrode or ion-sensitive field-effect transistor (ISFET). The enzyme sensor can be miniaturized and can accurately determine a concentration of glutamate even when it is low.

DETAILED DESCRIPTION OF THE INVENTION

Figure 1:
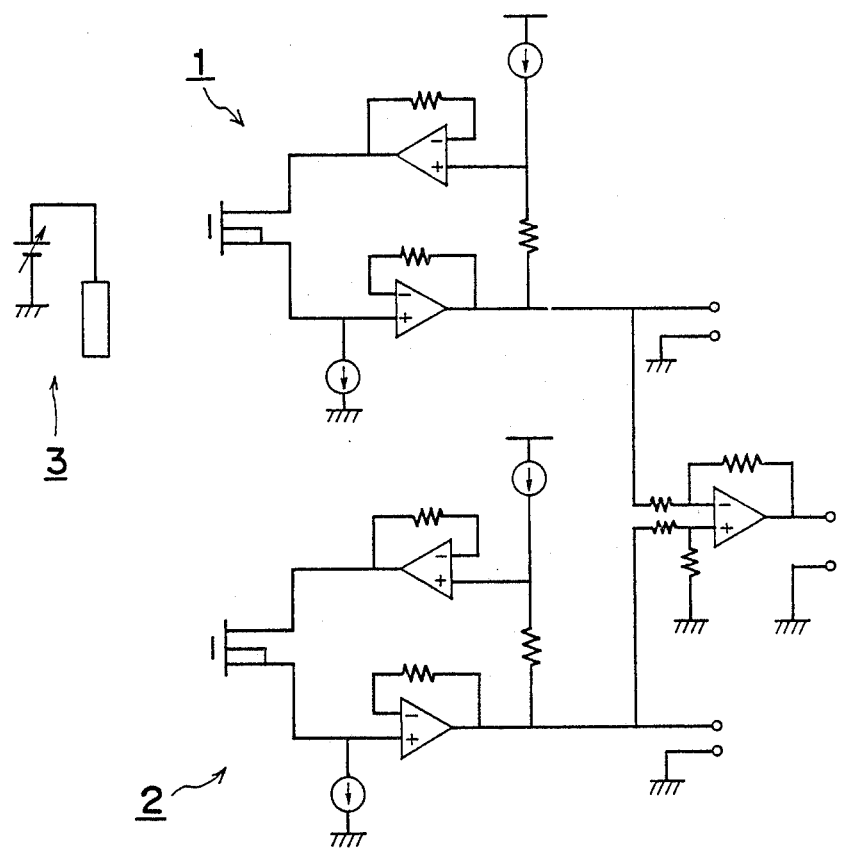
FIG. 1 shows a circuit drawing comprising an ion-sensitive field-effect transistor (ISFET) 1 on which glutamine synthetase is immobilized, an ion-sensitive field-effect transistor (ISFET) 2 on which glutamine synthetase is not immobilized and an Ag/AgCl electrode 3.

The pH glass electrode of the present invention includes a combination type electrode of a glass electrode and a comparative electrode, and a composite type electrode which is preferred for miniaturization. The ion-sensitive field-effect transistor (ISFET) can be any one which can determine a concentration of hydrogen ions. Preferred are silicon on sapphire (SOS)/ion-sensitive field-effect transistor (ISFET).

Glutamine synthetase employed in the present invention is not limited in supply sources and may be those produced from microorganisms, those produced from animals and so on. Preferred are those produced from microorganisms which most suitable growth temperature is in a range of 50° to 85° C. Examples of the microorganisms are Bacillus sp. such as *Bacillus stearothermophilus, Bacillus thermoproteolyticus, Bacillus acidocaldarius;* Thermoactinomyces sp.; Thermus sp.; Thermomicrobium sp. and the like. Typical examples of the microorganisms are *Bacillus stearothermophilus*, of which specific examples are ATCC 7933 strain (ATCC; The American Type Culture Collection, Maryland, U.S.A.), ATCC 7954 strain, ATCC 10194 strain, ATCC 12980 strain, NCA 1503 strain (NCA; National Canners' Association, Washington, CD.C., U.S.A.), UK 563 strain (PERM P-7275 strain, deposited at Fermentation Research Institute, Agency of Industrial Science and Technology, Ibaragi, Japan, on Sept. 29, 1983) and the like.

In the present invention, the enzyme sensor can be prepared by coating on the pH glass electrode or ion-sensitive field-effect transistor (ISFET) with a film shape water-insoluble carrier on which glutamine synthetase is immobilized. It is desirable for quick response that the thickness of the film is thin. For example, the thickness of the film is within the range of 1 to 100 micron, preferably 10 to 50 micron.

The immobilization of glutamine synthetase to the water-insoluble carrier can be carried out by a covalently bond method or a absorbed method, which are conventionally known as described in "Immobilized Enzyme" by Ichiro, Chibata, Kodan-sha (1975). It can also be carried out by a crosslinking method or an entrapped method.

The covalently bond method includes a peptide bond method, in which CNBr-activated agarose or dextran bonded with amino groups of glutamine synthetase; a diazo method, in which a water-insoluble carrier having aromatic amino groups is changed by nitrite to diazonium salts to which tyrosine residues of glutamine synthetase are coupled; a Schiff base method, in which a water-insoluble carrier having amino groups is bonded with glutaraldehyde and then to which amino groups of glutamine synthetase are bonded; and the like.

The absorbed method includes a method in which glutamine synthetase is immobilized on a water-insoluble carrier, such as DEAE-cellulose or phenoxyacetylcellulose and the like, with ion bond or physical force.

The crosslinking method includes a method in which glutamine synthetase and amino groups of albumin are crosslinked by glutaraldehyde to immobilize glutamine synthetase on albumin.

The entrapped method includes a method, in which a solution containing acrylamide monomers, a crosslinking agent (e.g. N,N'-methylenebisacrylamide), an initiator (e.g. riboflavin and peroxodisulfate), and a polymerization promoter (e.g. N,N,N',N'-tetramethylethylenediamine) is added to a glutamine synthetase solution and polymerized with light under a nitrogen blanket; a method in which glutamine synthetase is added to a collagenfibril suspension and dried; and the like.

For determining a concentration of L-glutamate by using the enzyme sensor of the present invention, a pH glass electrode or ion-sensitive field-effect transistor (ISFET) directly coated with an immobilized glutamine synthetase on a sensitive surface is immersed in a buffer solution containing an ammonium salt and adenosine-5'-triphosphate (ATP) and a pH change occurring from an addition of L-glutamate is detected. In this case, a pH change of $H^+$ produced by the following reaction is detected by a pH electrode or an ion-sensitive field-effect transistor (ISFET);

L-glutamate + $NH_4^+$ + Adenosine-5'-triphosphate (ATP)

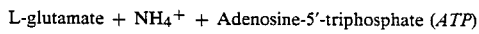
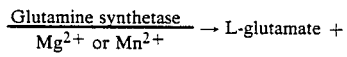

→ L-glutamate +

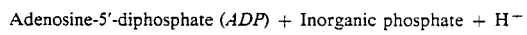

Adenosine-5'-diphosphate (ADP) + Inorganic phosphate + $H^-$

The preferred buffer solution for the determination contains 0.1 to 30 mM, preferably 0.5 to 10 mM of adenosine-5'-triphosphate (ATP), 0.5 to 50 mM, preferably 2 to 20 mM of an ammonium salt and 2 to 200 mM, preferably 2 to 100 mM of a magnesium or manganese salt. The buffer solution is prepared by dissolving adenosine-5'-triphosphate (ATP), the ammonium salt and the magnesium or manganese salt in a buffer solution (pH 4 to 10, preferably pH 5.5 to 9.5), such as preferably 3 to 100 mM of Tris-hydrochloric acid, imidazole-acetic acid and the like.

A temperature for the determination of the present invention is within a range of 5° to 75° C., preferably 15° to 55° C.

EXAMPLES

The present invention is illustrated by the following examples, which, however, are not to be construed as limiting the present invention to their details.

EXAMPLE 1

10 μl (1.4 units) of glutamine synthetase isolated from *Bacillus stearothermophilus* was mixed with 5 μl of 25 W/V % bovin serum albumin and 15 μl of 1 W/V % glutaraldehyde solution. 4 μl of the obtained mixture was added dropwise on a gate of an ion-sensitive field-effect transistor (ISFET) and air-dried at a temperature of 4° C. for a whole day and night to form an immobilized membrane. This was immersed into a 0.1M glycine-sodium hydroxide buffer solution at pH 8.5 for 15 minutes and rinsed with distilled water to obtain an ion-sensitive field-effect transistor (ISFET) having an oval shape of 0.15 mm×0.4 mm and a length of 5.5 mm, on which glutamine synthetase was immobilized.

The glutamine synthetase immobilized ion-sensitive field-effect transistor (ISFET) 1 and a non-immobilized ion-sensitive field-effect transistor (ISFET) 2 for control were immersed in a 25 ml of a reaction solution composed of 10 mM of Tris-hydrochloric acid buffer solution (pH 7.0), 7.6 mM of adenosine-5'-triphosphate (ATP), 10 mM of ammonium chloride and 50 mM of magnesium chloride. An Ag/AgCl electrode was immersed in the reaction solution for fixing a voltage of the solution. The ion-sensitive field-effect transistors (ISFET) formed the circuit shown in FIG. 1, wherein a voltage between source drains of the two ISFETs 1 and 2 set at 3.0 V and an applied voltage of the Ag/AgCl electrode was 6.5 V. When L-glutamate solution was added into the reaction solution at a boundary surface of the ISFET pH partially changes. The change was detected as a differential output between the two ISFETs. The temperature for the reaction was 30° C. and the reaction solution was kept stirring at 200 rpm.

Figure 2:
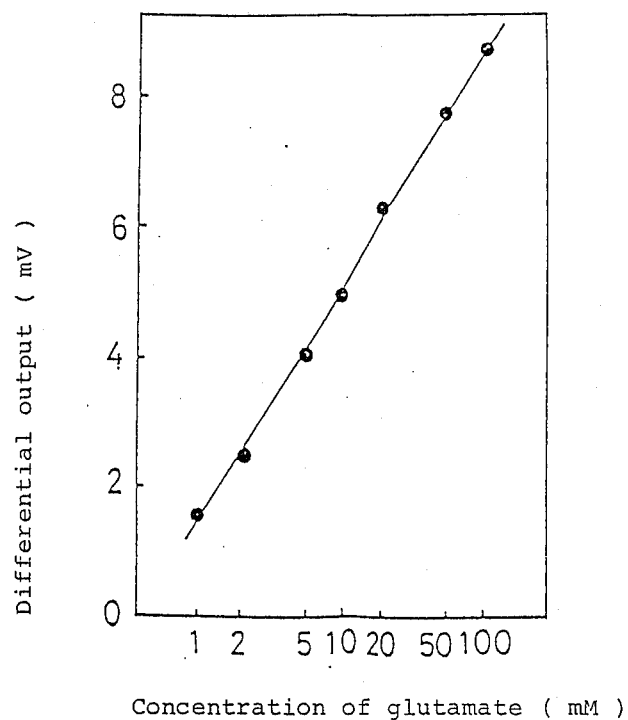
FIG. 2 is a drawing showing a relation between a concentration of glutamate and a differential output when an enzyme sensor of the present invention containing glutamine synthetase and ISFET is employed.

A concentration of the L-glutamate solution was adjusted to 1, 2, 5, 10, 20 and 50 mM and the relation between the L-glutamate concentration and the differential output was shown in FIG. 2. As is apparent from FIG. 2, the enzyme sensor exhibits good response properties in a concentration range of 1 to 50 mM. It has been found that the enzyme sensor of the present invention can effectively determine a concentration of L-glutamate. The response time was about 8 minutes.

COMPARATIVE EXAMPLE 1

A glutamate sensor composed of glutamine synthetase and an ammonia gas electrode was prepared as described in Denki Kagaku, 54, No. 3 (1986), pp. 290 to 291 and evaluated sensitivity in a low concentration range of L-glutamate.

Figure 3:
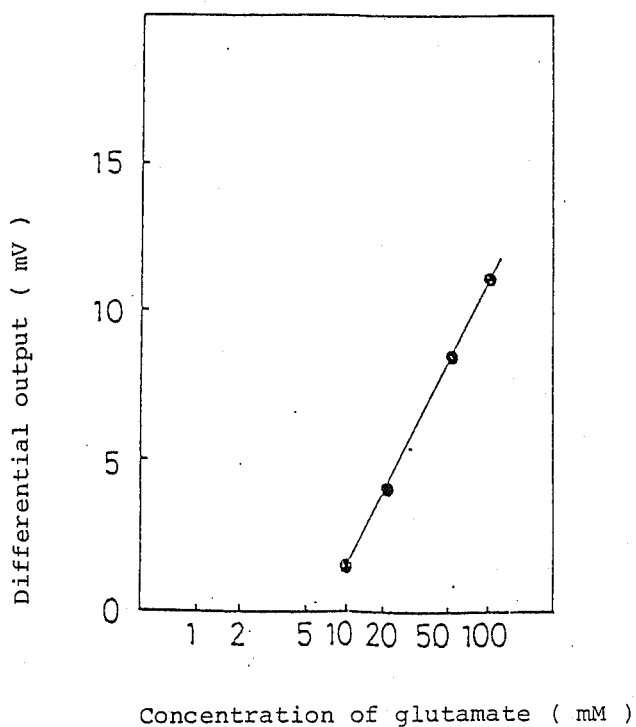
FIG. 3 is a drawing showing a relation between a concentration of glutamate and a differential output when a conventional enzyme sensor containing glutamine synthetase and an ammonia gas electrode is employed.

Thus, 0.04 mole of tolylene diisocyanate was reacted with 0.01 mole of polyethylene glycol at 80° C. for 30 minutes to form a urethane prepolymer. Then, 1.5 ml (15 units) of a glutamine synthetase solution was mixed with one gram of the melted urethane prepolymer at room temperature and allowed to foam, which was then spread on a glass plate to form an immobilized film. An ammonia gas electrode (Denki Kagaku Kogyo 7161-1P type) was covered with the immobilized film and then its electrode was setted up to pH meter (Denki Kagaku Kogyo HGC-10). A voltage change of the glutamate sensor was determined at 30° C. The size of the electrode has a diameter of 26 mm and a length of 17 cm. The buffer solution used in this example contained 7.6 mM of ATP, 10 mM of ammonium chloride, 50 mM of magnesium chloride, 50 mM of imidazole-hydrochloric acid and had pH 8.5. Concentrations of L-glutamate were 1, 2, 5, 10, 20, and 50 mM. FIG. 3 shows a relation between a concentration of L-glutamate and a voltage change.

As is apparent from FIG. 3, no response was seen within the range of not more than 10 mM.

EXAMPLE 2

Figure 4:
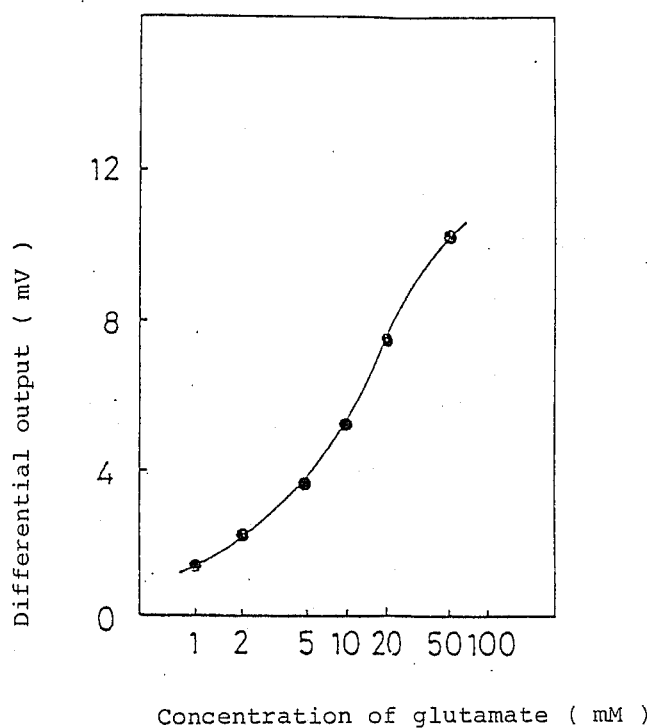
FIG. 4 is a drawing showing a relation between a concentration of glutamate and a differential output when another enzyme sensor of the present invention containing glutamine synthetase and a composite type pH glass electrode is employed.

0.04 mole of tolylene diisocyanate was reacted with 0.01 mole of polyethylene glycol at 80° C. for 30 minutes to form a urethane prepolymer. Then, 1.5 ml (15 units) of a glutamine synthetase solution was mixed with one gram of the melted urethane prepolymer at room temperature and allowed to foam, which was then spread on a glass plate to form an immobilized film. The immobilized film was covered on a composite type pH glass electrode (Central Kagaku Co. Ltd. SE-1600 GC) and a voltage change of the glutamate sensor was determined at 30° C. The size of the electrode has an oval shape of 4.5 mm×2 mm and a length of 3 cm. The buffer solution used in this example contained 7.6 mM of ATP, 10 mM of ammonium chloride, 50 mM of magnesium chloride, 10 mM of Tris-hydrochloric acid buffer solution and had pH 7.0. Concentrations of L-glutamate were 1, 2, 5, 10, 20, and 50 mM. FIG. 4 shows a relation between a concentration of L-glutamate and a voltage change.

What is claimed is:

1. An enzyme sensor for determining a concentration of glutamate comprising an immobilize enzyme acting specifically to a substrate and a transducer for converting the quantitative change of a substance or heat which is produced or consumed during an enzyme reaction to an electrical signal, wherein the enzyme is glutamine synthetase and the transducer is the pH glass electrode or ion-sensitive field-effect transistor.

2. The enzyme sensor according to claim 1 wherein glutamine synthetase is isolated from a microorganism having a most suitable growth temperature of 50° to 85° C.

* * * * *